US006825396B2

(12) United States Patent
MacArthur

(10) Patent No.: US 6,825,396 B2
(45) Date of Patent: *Nov. 30, 2004

(54) METHODS FOR TISSUE SPECIFIC SYNTHESIS OF PROTEIN IN EGGS OF TRANSGENIC HENS

(75) Inventor: William C. MacArthur, Ypsilant, MI (US)

(73) Assignee: Board of Trustees Operating Michigan State University, East Lansing, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/844,175

(22) Filed: Apr. 18, 1997

(65) Prior Publication Data

US 2003/0074681 A1 Apr. 17, 2003

Related U.S. Application Data

(60) Provisional application No. 60/019,641, filed on Jun. 12, 1996.

(51) Int. Cl.$^7$ ........................ A01K 67/00; C12N 15/85; C12N 15/00
(52) U.S. Cl. ........................ 800/19; 800/21; 435/325; 435/455
(58) Field of Search ........................ 800/23, 25, 19, 800/4, 8, 13, 21; 435/320.1

(56) References Cited

U.S. PATENT DOCUMENTS 4,650,764 A   3/1987  Temin et al.
5,162,215 A  11/1992  Bosselman et al.

OTHER PUBLICATIONS

Simkiss, "Transgenic birds," Animals with novel genes, Maclean, ed., Cambridge Univ. Press, New York, NY, pp. 1106–1137, 1994.*
Sang, Trends Biotech., vol. 12, pp. 415–420, Oct. 1994.*
Gaub et al. EMBO Journal, vol. 6, pp. 2313–2320, 1987.*
Bosselman et al. Science, vol. 243, pp. 533–535, Jan. 27, 1989.*
Jigami et al. Gene, vol. 43, pp. 273–279, 1986.*
Jost et al. Nucleic Acid Methylation, vol. 128, pp. 313–328, 1990.*
Olson et al., "Improved Self–Inactivating Retroviral Vectors Derived from Spleen Necrosis Virus," Journal of Virology 68(11): 7060–7066, 1994.
R. Dornburg, "Reticuloendotheliosis Viruses and Derived Vectors," Gene Therapy 2: 301–310, 1995.
Shuman et al., "Symposium: Molecular Approaches to Poultry Breeding. Gene Transfer by Avian Retroviruses," Poultry Science 65: 1437–1444, 1986.
Briskin et al., "Heritable Retroviral Transgenes Are Highly Expressed in Chickens," Proc. Natl. Acad. Sci. USA 88: 1736–1740, 1991.
Dougherty et al., "New Retrovirus Helper Cells With Almost No Nucleotide Sequence Homology to Retrovirus Vectors," Journal of Virology, 63(7): 3209–3212, 1989.

(List continued on next page.)

Primary Examiner—Michael Wilson
(74) Attorney, Agent, or Firm—Wilmer Cutler Pickering; Hale and Dorr LLP

(57) ABSTRACT

Vectors and methods are provided for introducing genetic material into cells of a chicken or other avian species. More particularly, vectors and methods are provided for transferring a transgene to an embryonic chicken cell, so as to create a transgenic hen wherein the transgene is expressed in the hen's oviduct and the transgene product is secreted in the hen's eggs and/or those of her offspring. In a preferred embodiment, the transgene product is secreted in the egg white.

7 Claims, 10 Drawing Sheets

OTHER PUBLICATIONS

Corthesy, B. et al., "Estrogen–Dependent in Vitro Transcription from the Vitellogenin Promoter in Liver Nuclear Extracts," *Science* 239:1137–1139 (1988).

Ktistaki, E. et al., "Transcriptional regulation of the apolipoprotein A–IV gene involves synergism between a proximal orphan receptor response element and a distant enhancer located in the upstream promoter region of the apolipoprotein C–III gene," *Nucleic Acids Research* 22(22):4689–4696 (1994).

Wasylyk, B. et al., "Short and long range activation by the SV–40 enhancer," *Nucleic Acids Research* 12(14):5589–5608 (1984).

Bosselman, R.A., et al., "Germline Transmission Of Exogenous Genes In The Chicken," *Science* 243:533–535 (1989).

Bradshaw, M.S., et al., "Far Upstream Ovalbumin Enhancer Binds Nuclear Factor–1–like Factor," *J. Biol. Chem.* 263(17):8485–8490 (1988).

Bradyopadhy, P.K., et al., "Expression Of Complete Chicken Thymidine Kinase Gene Inserted In A Retrovirus Vector," *Mol. Cell Biol.* 4(4):749–754 (1984).

Carscience, et al., "Germline Chimeric Chickens From Dispersed Donor Blastodermal Cells And Compromised Recipient Embryos," *Development* 117:669–675 (1993).

Crittenden et al., "Transgenic Livestock Models In Medicine And Agriculture," pp. 73–87 (Wiley–Liss (1990)).

Curran, T., et al., "Fos and Jun: The AP–1 Connection," *Cell* 55:395–397 (1988).

Davis, et al., "Single Chain Antibody (SCA) Encoding Genes: One–Step Construction And Expression In Eukaryotic Cells," *Biotechnol.* 9:165–169 (1991).

Dierich, A., et al., "Cell–Specificity Of The Chicken Ovalbumin And Conalbumin Promoters," *EMBO Journal* 6(8):2305–2312 (1987).

Emerman, M., et al., "Genes With Promoters In Retrovirus Vectors Can Be Independently Suppressed By An Epigenetic Mechanism," *Cell* 39:459–467 (1984).

Emerman, M., et al., "High–Frequency Deletion In Recovered Retrovirus Vectors Containing Exogenous DNA With Promoters," *J. Virology* 50(1):42–49 (1984).

Etches, et al., "Chimeric Chickens And Their Use In Manipulation Of The Chicken Genome," *Poultry Science* 72:882–889 (1993).

Evans, M.I., et al., "A Somatomedin–Like Peptide Hormone Is Required During The Estrogen–Mediated Induction Of Ovalbumin Gene Transcription," *Cell* 25:187–193 (1981).

Evans, M.I., et al., "Regulation Of The Ovalbumin Gene: Effects Of Insulin, Adenosine 3',5'–Monophosphate, And Estrogen," *Endocrinology* 115(1):368–377 (1984).

Gaub, M.P., et al., "Activation Of The Ovalbumin Gene By The Estrogen Receptor Involves The Fos–Jun Complex," *Cell* 63:1267–1276 (1990).

Helig, R., et al., "The Ovalbumin Gene Family—The 5' End Region Of The X and Y Genes," *J. Mol. Biol.* 156:1–19 (1982).

Houdebine, L.M., "Production Of Pharmaceutical Proteins From Transgenic Animals," *J. Biotechnology* 34:269–287 (1984).

Jigami, Y., et al., "Expression Of Synthetic Human–Lysozyme Gene In *Saccharomyces cerevisiae*: Use Of A Synthetic Chicken–Lysozyme Signal Sequence For Secretion And Processing," *Gene* 43:273–279 (1986).

Kato, S., et al., "A Far Upstream Estrogen Response Element Of The Ovalbumin Gene Contains Several Half–Palindromic 5'–TGACC–3' Motifs Acting Synergistically," *Cell* 68:731–742 (1992).

Kaye, J.S., et al., "Steroid Hormone Dependence Of Four DNase I–Hypersensitive Regions Located Within The 7000–bp 5'–Flanking Segment Of The Ovalbumin Gene," *EMBO J.* 5(2):277–285 (1986).

Klein–Hitapass, L., et al., "Synergism Of Closely Adjacent Estrogen–Responsive Elements Increases Their Regulatory Potential," *J. Mol. Biol.* 201:537–544 (1988).

Kozak, M., et al., "An Analysis Of Vertebrate mRNA Sequences: Intimations Of Translational Control," *J. Cell Biol.* 115(4):887–903 (1991).

LeMeur, M.A., et al., "Termination Of The Ovalbumin Gene Transcription," *EMBO Journal* 3(12):2779–2786 (1994).

Lilley, et al., "Recombinant Single–Chain Antibody Peptide Conjugates Expressed In *Escherichia coli* For The Rapid Diagnosis Of HIV," *J. Immunol. Meth.* 171:211–226 (1994).

Love, J., et al., "Transgenic Birds By DNA Microinjection," *Biotechnology* 12:60–63 (1994).

O'Hare, K., et al., "No More Than Seven Interruptions In The Ovalbumin Gene: Comparison Of Genomic And Double–Stranded cDNA Sequences," *Nucleic Acids Research* 7(2):321–334 (1979).

Petropoulos, C.J., et al., "Replication–Competent Retrovirus Vectors For The Transfer And Expression Of Gene Cassettes In Avian Cells," *J. Virol.* 65:3728–3737 (1991).

Petropoulos, C.J., et al., "Using Avian Retroviral Vectors For Gene Transfer," *J. Virol.* 66(6):3391–3397 (1992).

Ponglikitmongkol, M., et al., "Synergistic Activation Of Transcription By The Human Estrogen Receptor Bound To Tandem Responsive Elements," *EMBO Journal* 9(7):2221–2231 (1990).

Robinson, A., et al., "Isolation And Properties Of The Signal Region From Ovalbumin," *FEBS* 203(2):243–246 (1986).

Sagami, I., et al., "Identification Of Two Factors Required For Transcription Of The Ovalbumin Gene," *Mol. Cell. Biol.* 6(12):4259–4267 (1986).

Schweers, L., et al., "A Protein With A Binding Specificity Similar To $NF-_{\kappa}B$ Binds To A Steroid–Dependent Regulatory Element In The Ovalbumin Gene," *J. Biol. Chem.* 266(16):10490–10497 (1991).

Sevoian, et al., "Avian Lymphomatosis. VI. A Virus Of Unusual Potency And Pathogenicity," *Avian Dis* 8:336–347 (1964).

Shuman, et al., "Symposium: Molecular Approaches To Poultry Breeding—Gene Transfer By Avian Retroviruses," *Poultry Science* 65:1437–1444 (1986).

Tsai, S.Y., et al., "Cooperative Binding Of Steroid Hormone Receptors Contributes To Transcriptional Synergism At Target Enhancer Elements," *Cell* 57:443–448 (1989).

von Heijne, G., "Patterns Of Amino Acids Near Signal–Sequence Cleavage Sites," *Eur. J. Biochem.* 133:17–21 (1983).

von Heijne, G., "How Signal Sequences Maintain Cleavage Specificity," *J. Mol. Biol.* 173:243–251 (1984).

von Heijne, G., "Signal Sequences—The Limits Of Variation," *J. Mol. Biol.* 184:99–105 (1985).

Wang, L., et al., "COUP Transcription Factor Is A Member Of The Steroid Receptor Superfamily," *Nature* 340:163–166 (1989).

Watanabe, S., et al., "Construction Of A Helper Cell Line For Avian Reticuloendotheliosis Virus Cloning Vectors," *Mol. Cell. Biol.* 3(12):2241–2249 (1983).

\* cited by examiner transfect C3 cells

```
Ssp BI            met arg ser leu leu ile leu val leu cys phe leu pro leu
5'GTACATACAGCT    ATG AGG TCT TTG CTA ATC TTG GTG CTT TGC TTC CTG CCC CTG
3'   TATGTCGA    TAC TCC AGA AAC GAT TAG AAC CAC GAA ACG AAG GAC GGG GAC -1  +1   Cla I
              ala ala leu gly asn ile
              GCT GCT CTG GGG AAT AT      3'
              CGA CGA GAC CCC TTA TAG C   5'
```

METHODS FOR TISSUE SPECIFIC SYNTHESIS OF PROTEIN IN EGGS OF TRANSGENIC HENS

RELATED APPLICATIONS

This application is a continuation-in-part of U.S. Application Serial No. 60/019,641, entitled "Vector For Expression Of Proteins Into Eggs Of Transgenic Hens," filed Jun. 12, 1996.

FIELD OF THE INVENTION

The present invention relates generally to vectors and methods for introducing genetic material into an embryo of a chicken and other avian species and, more particularly, to vectors and methods for transferring a gene of interest to an embryonic chicken cell, so as to create a transgenic hen having the gene of interest expressed in the hen's oviduct and the gene product secreted in the hen's eggs and/or those of her offspring.

BACKGROUND OF THE INVENTION

Since the development of recombinant DNA technology some twenty-five years ago, the prospect of producing proteins on a large scale, rather than extracting them from tissue where they are naturally expressed, has become a reality. In particular, over the last two decades, progress in the development of expression vectors has led to the production of thousands of recombinant proteins on a laboratory scale. Production of commercial quantities of recombinant proteins requires often difficult and expensive scaling up procedures, but has nonetheless also been successful. In addition, transgenic animals including mice, rabbits, pigs, sheep, goats and cows have been engineered to produce human pharmaceuticals in their tissues or secretions. Houdebine, L. M., *J. Biotechnology* 34:269–287 (1994).

Although egg white is thought to be an excellent host for recombinant protein production, preparing transgenic avians has proven to be technically difficult due in large part to problems involved in manipulating the chicken embryo. When oviposition occurs, the embryo has already reached a stage corresponding to a mammalian late blastula or early gastrula. Genetic manipulation of the embryo during earlier development requires reintroduction to the female or in vitro culture, both difficult procedures. Houdebine, L. M., *J. Biotechnology* 34:269–287 (1994). Despite these difficulties, transgenic chickens have been produced that are resistant to infection by avian leukosis (Crittenden and Salter, "Transgenic Livestock Models In Medicine And Agriculture" pp. 73–87 (Wiley-Liss (1990))), or have high levels of circulating growth hormone. Bosselman, R. A., et al., *Science* 243:533–535 (1989).

Four general methods for generating transgenic avians have been reported. One method involves excision of a developing egg from the oviduct, microinjection of DNA near the blastoderm, and in vitro culture of the manipulated embryo in solution and surrogate shells. Love, J., et al., *Biotechnology* 12:60–63 (1994). A second method requires the culture and transfection of primordial germ cells, with subsequent transplantation into an irradiated recipient near the same stage of development as the donor. Carsience et al., *Development* 117:669–675 (1993); Etches et al., *Poultry Science* 72:882–889 (1993). Although technically very demanding, these two approaches are attractive because large pieces of DNA can be transferred.

A third method involves blind injection of replication competent retrovirus with a needle near the blastoderm of a newly laid egg. Petropoulos, C. J., et al., *J. Virol.* 65:3728–3737 (1991). Although this method is the simplest, it is also limited in that the DNA to be transferred must be approximately 2 kb or less in size and, the method results in viremic hens which shed infective recombinant retrovirus. Petropoulos, C. J., et al., *J. Virol.* 66(6):3391–3397 (1992).

The fourth method involves a replication-defective retroviral vector system (see, e.g., U.S. Pat. Nos. 5,162,215 and 4,650,764, hereby incorporated by reference). One of these systems (Watanabe and Temin, *Mol. Cell. Biol.* 3(12):2241–2249 (1983)) has been derived from the reticuloendotheliosis virus type A (REV-A). Sevoian et al., *Avian Dis.* 8:336–347 (1964). Replication-defective retroviral vectors derived from the REV-A virus are based on the helper cell line C3 (Watanabe and Temin, *Mol. Cell. Biol.* 3(12):2241–2249 (1983)) which contains the components of a packaging defective helper provirus. The derivation of the C3 helping line and several replication-defective retroviral vectors have been described in detail in U.S. Pat. No. 4,650,764 and Watanabe and Temin, *Mol. Cell Biol.* 3(12):2241–2249 (1983). This method is more technically demanding than the replication competent technique in that the blastoderm must be exposed, and microinjection equipment must be used. Bosselman, R. A., et al., *Science* 243:533–535 (1989). Nonetheless, it results in transgenic hens free of replication competent retrovirus, and can transfer DNA as large as 8 kb in size.

Tissue specific expression of a foreign gene in a transgenic chicken was achieved using the replication competent retrovirus technique. Petropoulos, C. J., et al., *J. Virol.* 66(6):3391–3397 (1992). A replication competent retrovirus was used to deliver the reporter gene chloramphenicol acetyl transferase (CAT), driven by a muscle specific promoter, a action, to skeletal muscle. Tissue specific expression of a recombinant protein in the egg of a transgenic avian has not yet been successful.

It would thus be desirable to provide a vehicle and method for transferring a gene to an embryonic chicken cell (or other avian species) so as to create a transgenic hen wherein the gene is expressed in a tissue specific manner. It would also be desirable to provide a vehicle and method for transferring a gene to an embryonic chicken cell, wherein the gene is expressed in the hen's oviduct and secretion of the gene product is in the hen's eggs. It would also be desirable to provide a vehicle and method for transferring a gene to an embryonic chicken cell, wherein the gene is expressed in the hen's oviduct and secretion of the gene product is in the hen's eggs without compromise to the hen's health and the health of other birds in contact with her.

SUMMARY OF THE INVENTION

Vectors and methods are provided for introducing genetic material into cells of a chicken or other avian species. More particularly, vectors and methods are provided for transferring a transgene to an embryonic chicken cell, so as to create a transgenic hen wherein the transgene is expressed in the hen's oviduct and the transgene product is secreted in the hen's eggs and/or those of her offspring. In a preferred embodiment, the transgene product is secreted in the egg white.

In one embodiment, the vector comprises a portion of a retroviral genome, capable of transfecting a cell and incapable of replication, i.e., a replication-defective retroviral vector. The vector further comprises a transgene, operatively-linked to appropriate control elements such that the transgene may be expressed in a tissue specific manner.

In one embodiment, the control elements include an enhanced promoter directing the expression of the transgene in the oviduct, an untranslated region 5' to the structural gene (coding region) of appropriate length and sequence to promote efficient translation, and a signal sequence directing the secretion of the transgene product in the egg white. In this embodiment, the promoter may be chosen, without limitation, from the group consisting of ovalbumin, lysozyme, conalbumin and ovomucoid promoters, and combinations thereof. In another embodiment, the control sequences include a promoter directing the expression of the transgene in the liver and a signal sequence directing the uptake and secretion of the transgene product into the egg yolk. In this embodiment, the promoter may be chosen, without limitation, from the group consisting of vitellogenin and apolipoprotein A promoters, and combinations thereof.

The vectors of the present invention may be used in producing transgenic avians, particularly chickens, by methods known to those skilled in the art, such as the four methods described above (see, Background Of The Invention). For example, as described in U.S. Pat. No. 5,162,215, herein incorporated by reference, the vectors may be used to introduce a nucleic acid sequence, e.g., a gene, into germ cells and stem cells of an embryo of a chicken. In one embodiment, a retrovirus generated from the vector is microinjected in a newly laid chicken egg, in close proximity to (e.g., directly beneath) the blastoderm The egg is then sealed and incubated until the chicken is hatched from the egg. The chimeric chicken is then tested for expression of the transgene and if positive and the chicken is female (hen), the eggs of the chicken arc harvested and the protein is isolated by methods known to those skilled in the art. If the chicken is male (rooster), it can be bred to produce a female transgenic chicken whose eggs may then be harvested. Transgenic avians and eggs, as well as methods of making transgenic avians and eggs, are thus provided.

Other features and advantages of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

Figure 1:
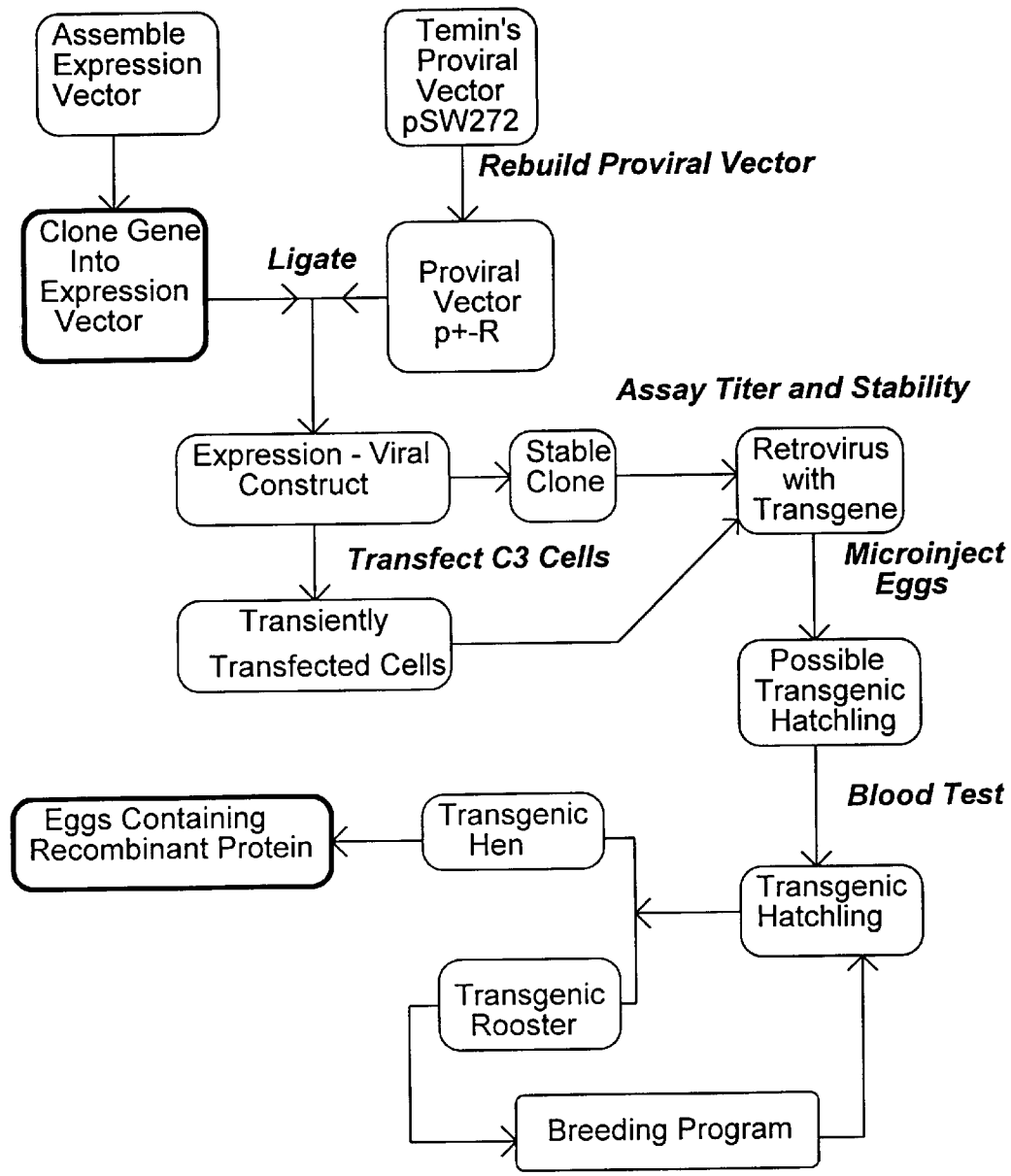
FIG. 1 is a schematic illustrating the production of the vectors of the present invention and methods of using same to produce transgenic chickens.

Vectors and methods are provided for introducing genetic material into cells of a chicken or other avian species. More particularly, vectors and methods are provided for transferring a transgene to embryonic chicken cells, so as to create a transgenic hen wherein the transgene is expressed in the hen's oviduct and the transgene product is secreted in the hen's eggs and/or those of her offspring. FIG. 1 is a schematic illustrating the methods of the present invention, including vector production and use to produce a transgenic chicken.

In one embodiment, the vector comprises a portion of a retroviral genome, capable of transfecting a cell and incapable of replication, i.e., a replication-defective retroviral vector. Replication-defective retroviral vectors derived from the REV-A virus are preferred. The vector further comprises a gene of interest also referred to herein as a transgene, operatively-linked to appropriate control elements such that the transgene product may be synthesized in a tissue specific manner.

Figure 2:
FIG. 2 is a schematic illustrating a preferred vector of the present invention.

A schematic of a preferred expression vector of the present invention is set forth in FIG. 2. It will be appreciated that the 3 kb β-galactosidase gene shown in FIG. 2 is merely a reporter gene and is replaced with any transgene(s) or fragment thereof. For example a gene which encodes a blood clotting protein such as fVIII, may be employed. The transgene product or protein, is secreted in the egg and then isolated. Once purified, the protein may be used in pharmaceutical applications such as in the treatment of hemophilia. Other preferred genes include, without limitation, the genes encoding blood proteins including human serum albumin and α 1-antitrypsin, hematopoietic growth factors including erythropoietin, and lymphopoietic growth factors such as granulocyte colony stimulating factors. Genes encoding industrial proteins such as α-amylase and glucose isomerase may also be employed. Moreover, genes encoding antibodies and immunoreactive portions thereof, may also be included in the vectors of the present invention (see, e.g., Lilley, et al., *J. Immunol. Meth.* 171:211–226 (1994) and Davis et al., *Biotechnol.* 9:165–169 (1991), herein incorporated by reference).

The gene, or a fragment of the gene, to be transferred may be produced and purified by any of several methods well known in the art. Thus, a gene can be produced synthetically, or by treating mRNA derived from the transcription of the gene with a reverse transcriptase so as to produce a cDNA version of the gene, or by the direct isolation of the gene from a genomic bank or from other sources.

Control elements which flank the transgene include promoters and enhancers, UTRs and signal sequence(s), that allow tissue specific expression of the transgene. In one embodiment, the promoter directs expression of the transgene in the oviduct of the transgenic avian. A preferred promoter of the present invention is chosen from the group consisting of ovalbumin, lysozyme, conalbumin and ovomucoid promoters, and combinations thereof. Signal sequences included in the vector direct secretion of the transgene product into the egg white. In an alternative embodiment, the promoter drives expression of the transgene in the liver and signal sequences included in the vector direct the secretion and uptake of the transgene product into the egg yolk. In this embodiment, the promoter is chosen from the group consisting of vitellogenin and apolipoprotein A promoters, and combinations thereof. Preferred enhancers are viral enhancers including, but not limited to, the SV40 enhancer, or portion thereof. Lysozyme enhancers may also be employed in addition to synthetic DNAs thought to bind transcription factors, such as a steroid hormone response element, e.g., the tandem EREs described herein.

In one embodiment of the present invention, shown in FIG. 2, control elements which flank the gene of interest include the SV40 enhancer, three tandem estrogen response elements (ERE), 1.3 kb of the ovalbumin promoter (5' flank), 77 bp of 5' untranslated region (UTR), the N-terminal signal peptide sequence from the chicken lysozyme gene, and the polyadenylation and termination signals from the SV40 small T antigen. (SEQ ID No. 1) sets forth the nucleotide sequence of the preferred construct. In a preferred embodiment of the present invention, this construct is contained on a 5 kb Xba I fragment which is inserted into a replication-defective retroviral vector for transgenesis. The preferred proviral vector is a derivative of plasmid pSW272. Emerman, M., et al., *Cell* 39:459–467 (1984); U.S. Pat. No. 4,650,764. As described in U.S. Pat. No. 4,650,764, herein incorporated by reference, cell lines have been constructed to complement these vectors and produce the viral proteins necessary to package replication-defective retroviral vectors. The packaged vector may infect a cell once, but is incapable itself of subsequent rounds of infection.

The vectors of the present invention are particularly useful in producing transgenic avians, particularly chickens, by methods known to those skilled in the art. For example, as described in U.S. Pat. No. 5,162,215, herein incorporated by reference, the vectors may be used to introduce a nucleic acid sequence, e.g., a gene, into cells of an embryo of a chicken. In one embodiment, a retrovirus generated from the vector is microinjected in a newly laid chicken egg arrested at stage X (not generally more than seven days old, unincubated), in close proximity to, e.g., directly underneath, the blastoderm. More specifically, an opening about 5 mm in diameter is made in the side of the egg, normally by the use of a drilling tool fitted with an abrasive rotating tip which can drill a hole in the eggshell without damaging the underlying shell membrane. The membrane is then cut out by use of a scalpel or 18 gauge needle and thumb forceps, so that a portion of the shell and membrane is removed thereby exposing the embryo. The embryo is visualized by eye or with an optical dissecting microscope with an 6x–50x magnification. A solution, usually tissue culture medium, containing the retrovirus of the present invention, is microinjected into an area beneath and around the blastoderm, using a micro-manipulator and a very small diameter needle, preferably glass, 40–60 $\mu$M outer diameter at the tip, 1 mm outer diameter along it's length. The volume of solution for microinjection is preferably 5–20 $\mu$l. After microinjection, the egg is sealed with shell membrane and a sealing material, preferably glue or paraffin. The sealed egg is then incubated at approximately 38° C. (99.5° F.) for various time periods up to and including the time of hatching to allow normal embryo growth and development. DNA from embryos and from newly hatched chicks is tested for the presence of sequences from the microinjected retrovirus. The presence of the inserted sequences is detected by means know in the art and appropriate to the detection of the specific gene or if desirable, gene product if the gene or gene product, i.e., protein, is present, eggs from the chimeric chicken are collected and the protein isolated.

In another embodiment, the vector or transfected cells producing the virus containing the transgene is injected into developing oocytes in vivo, for example, as described in Shuman and Shoffner, *Poultry Science* 65:1437–1444 (1986), herein incorporated by reference. The same steps of incubation, hatching, etc. are followed.

As referred to herein, by the term "gene" or "transgene" is meant a nucleic acid, either naturally occurring or synthetic, which encodes a protein product. The term "nucleic acid" is intended to mean natural and/or synthetic linear, circular and sequential arrays of nucleotides and nucleosides, e.g., cDNA, genomic DNA (gDNA), mRNA, and RNA, oligonucleotides, oligonucleosides, and derivatives thereof. The phrase "operatively-linked" is intended to mean attached in a manner which allows for transgene transcription. The term "encoding" is intended to mean that the subject nucleic acid may be transcribed and translated into either the desired polypeptide or the subject protein in an appropriate expression system, e.g., when the subject nucleic acid is linked to appropriate control sequences such as promoter and enhancer elements in a suitable vector (e.g., an expression vector) and when the vector is introduced into an appropriate system or cell. As used herein, "polypeptide" refers to an amino acid sequence which comprises both full-length protein and fragments thereof.

The term "replication-defective retroviral vector" refers to a vector comprising a portion of a retroviral genome capable of infecting a cell but incapable of unrestricted replication, i.e., multiple rounds of infection, usually due to mutations or deletions in the virus genome. The term "REV-derived replication-defective vector" refers to a reticuloendotheliosis viral vector that is incapable of unrestricted replication.

The term "avian species" includes, without limitation, chicken, quail, turkey, duck and other fowl. The term "hen" includes all females of the avian species. A "transgenic avian" generally refers to an avian that has had a heterologous DNA sequence, or one or more additional DNA sequences normally endogenous to the avian (collectively referred to herein as "transgenes") chromosomally integrated into the germ cells of the avian. As a result of such transfer and integration, the transferred sequence may be transmitted through germ cells to the offspring of a transgenic avian. The transgenic avian (including its progeny) will also have the transgene fortuitously integrated into the chromosomes of somatic cells.

In order to more fully demonstrate the advantages arising from the present invention, the following examples are set forth. It is to be understood that the following is by way of example only and is not intended as a limitation on the scope of the invention.

SPECIFIC EXAMPLE 1

Vector Construction

Discussion

Promoter. The protein ovalbumin is the most abundant protein in egg white. Ovalbumin is synthesized in the tubular gland cells of the oviduct magnum and secreted directly into the lumen, where it joins the forming egg. The ovalbumin promoter is a well characterized and complex promoter. Houdebine, L. M., *J. Biotech* 34:269–287 (1994). The ovalbumin promoter is regulated by all known classes of steroid hormones (Gaub, M. P., et al., *Cell* 63:1267–1276 (1990)), and at least eight different regulatory proteins or groups of proteins are thought to bind to a region spanning 1.1 kb 5' to the cap site. These proteins include the TATA binding protein complex (TFIID), the estrogen receptor, activator protein 1 (AP-1), which includes the fos and jun gene products and related peptides (Curran, T., et al., *Cell* 55:395–397 (1988)), the chicken ovalbumin upstream promoter transcription factor (COUP-TF) (Wang, L., et al., *Nature* 340:163–166 (1989)) and an associated protein S300-II (Sagami, I., et al., *Mol. Cell. Biol.* 6(12):4259–4267 (1986)), a NF-$_K$B-like nuclear protein (Schweers, L., et al., *J. Biol. Chem.* 266(16):10490–10497 (1991)), and a nuclear factor I (NF-I) homolog. Bradshaw, M. S., et al., *J. Biol. Chem.* 263(17):8485–8490 (1988). The cis acting sequences responsible for these interactions are included in the 1.3 kb fragment used as the preferred promoter in the present invention. Although the natural system of ovalbumin expression was mimicked as closely as possible in the vectors and methods of the present invention, the ovalbumin 5' regulatory region spans some 8 kb (Gaub, M. P., et al., *Cell* 63:1267–1276 (1990)), which, together with the other downstream elements (LeMeur, M. A., et al., *EMBO Journal* 3(12):2779–2786 (1994)), is too large for a replication-defective retroviral vector. Emerman, M., et al., *Cell* 39:459–467 (1984). Thus, the 1.3 kb fragment was used. However, it will be appreciated by those skilled in the art, that the ovalbumin promoter may include any portion of the ovalbumin transcription unit capable of driving expression of a transgene in the oviduct. Moreover, although the ovalbumin promoter is discussed in detail herein, it will be appreciated that other promoters that drive expression in cells generating the egg white may be employed, including but not limited to, lysozyme, conalbumin and ovomucoid promoters, and combinations thereof.

In an alternative embodiment, a promoter which drives expression of the transgene in the liver is employed, such as the vitellogenin or apolipoprotein A promoter, and combinations thereof. Although vitellogenin and apolipoprotein A are very abundant proteins in the yolk, they are synthesized in the liver and are then transported to the yolk through the blood. It is deposited in the yolk via a specific receptor which recognizes an N-proximal fragment of the vitellogenin precursor. Thus, the vectors of the present invention, when containing the vitellogenin or apolipoprotein A promoters (or combinations thereof), they also contain a signal sequence or separate sequences directing the secretion and uptake of the protein in the yolk. Although a blood-borne intermediate step is required, this type of vector is useful particularly for antibody production or compounds found in blood of other species.

Enhancer. The SV40 enhancer has been previously used to increase expression from the ovalbumin promoter. Dierich, A., et al., *EMBO Journal* 6(8):2305–2312 (1987). AP-1 has been shown to act on the proximal portion of the ovalbumin promoter, and the SV40 enhancer may increase the local concentration of the AP-1 complex or some of its components. Curran, T., et al., *Cell* 55:395–397 (1988). There are other control elements found in the ovalbumin 5' flank which are not included in the 1.3 kb ovalbumin promoter. Kaye et al., *EMBO Journal* 5(2):277–285 (1986), discovered four hormone dependent DNAase I hypersensitive sites in the 5' flank of ovalbumin chromatin which are correlated with expression of the ovalbumin gene. Two sites are contained within the preferred promoter used herein, and the other two lie 3.3 kb and 6 kb 5' to the cap site (sites III and IV respectively). Site III, at −3.3 kb is contained on a 675 bp Pst I-Xba I fragment from approximately 3.7 kb to 3.1 kb 5' to the cap site. Within this fragment are four half palindromic estrogen response elements (EREs) which enhance expression from the ovalbumin promoter in a synergistic fashion. Kato, S., et al., *Cell* 68:731–742 (1992). The half EREs are spaced more than 100 base pairs apart from each other. Nonetheless, fusion and deletion studies have shown both the functionality and necessity of these elements in conferring estrogen responsiveness to a truncated ovalbumin promoter. Kato, S., et al., *Cell* 68:731–742 (1992). It is thought that several weakly bound estrogen receptors interact synergistically at this locus to result in more stable receptor-DNA complexes, which then either destabilize the helix, or increase the local concentration of transcription factors in the vicinity of the promoter.

This region III fragment is not included in the preferred vector of the present invention, but instead is replaced by a synthetic oligonucleotide containing a full palindromic ERE adjacent and 5' to a single ERE. The estrogen receptor binds palindromic EREs as a dimer with much greater affinity than to a single half site. The tandem arrangement of palindromic ERE and a single ERE spaced seven base pairs away adds even further stability. Klein-Hitapaβ, L., et al., *J. Mol. Biol.* 201:537–544 (1988). It is thought that this oligonucleotide functionally replaces the −3.3 kb hypersensitive site in vivo.

It is likely that the tandem EREs have a positive effect on gene expression. EREs have been shown to enhance expression in estrogen responsive cells, and with promoters containing imperfect EREs. Tsai, S. Y., et al., *Cell* 57:443–448 (1989); Ponglikitmongkol, M., et al., *EMBO Journal* 9(7):2221–2231 (1990). There are imperfect EREs in the ovalbumin promoter, and it is likely that a synergism occurs between the synthetic perfect consensus EREs and the natural ones.

The hormone dependent DNAase I hypersensitive site at −6 kb is contained within 1.2 kb. Fusion studies with this DNA fragment show no evidence of estrogen responsive enhancement of the ovalbumin promoter. Kato, S., et al., *Cell* 68:731–742 (1992). For this reason, no part or analog was included in the vector shown in FIG. 2.

Previous investigators have demonstrated an absolute requirement for an intracellular phosphorylation cascade; via somatomedin, insulin, or cAMP for induction of the ovalbumin gene in response to estrogen. Evans, M. I., et al., *Cell* 25:187–193 (1981); Evans, M. I., et al., *Endocrinology* 115(1):368–377 (1984). Although these studies are more than ten years old and the intracellular second messenger cascade mechanisms are now understood in greater detail, the exact mechanism with respect to specific cis acting sequences in the ovalbumin promoter has not been demonstrated definitely. It is not unreasonable to suggest, however, that the mechanism involves AP-1 binding, the cis acting sequence of which is included in both the preferred ovalbumin promoter and the SV40 enhancer. Curran, T., et al., *Cell* 55:395–397 (1988).

5' Untranslated Region. The 5' untranslated region (UTR) is that of ovalbumin RNA. The ovalbumin gene contains a 5' leader exon that is spliced to the first coding exon to generate an untranslated region 65 bases in length. O'Hare, K., et al., *Nucleic Acids Research* 7(2):321–334 (1979). The vector UTR sequence is copied almost exactly off the cDNA to yield a 5' UTR that very closely resembles that of ovalbumin RNA. The only difference is a one base mutation near the 5' end which was necessary for construction, and an additional 3' linker, resulting in a UTR 77 bp in length. A 77 base leader is more consistent with Kozak's study which suggest that a minimum of 77 bases is required for maximum translational efficiency (Kozak, M., et al., *J. Cell Biol.* 115(4):887–903 (1991)), however, any UTR with a functional sequence around the start codon may be used.

Signal Sequence. The signal peptide is responsible for transport of the protein out of the cell, and signal peptide sequence theory is well developed. von Heijne, G., *Eur. J. Biochem.* 133:17–21 (1983); von Heijne, G., *J. Mol. Biol.* 173:243–251 (1984); and von Heijne, G., *J. Mol. Biol.* 184:99–105 (1985). In the majority of secreted proteins, the sequence is at the N-terminus of the nascent protein and is cleaved during synthesis and translocation into the endoplasmic reticulum. In the case of ovalbumin, however, the sequence is internal to the protein and is not cleaved (Robinson, A., et al., *FEBS* 203(2):243–246 (1986)), thus rendering it inappropriate for use in an expression vector. The signal sequence of egg white lysozyme was used in the vectors of the present invention as a translocation signal because it is a cleaved N-terminal sequence, it functions in vivo in the chicken oviduct, and will release a protein with a native N-terminus in Saccharomyces. Jigami, Y., et al., *Gene* 43:273–279 (1986). However, it will be appreciated by those skilled in the art that any signal sequence(s) may be used.

Gene. The β-galactosidase gene was utilized in the vector set forth in FIG. 2 for two reasons. First, at 3 kb, it is the largest of the available reporter genes; many genes encoding commercially valuable proteins are much smaller than this. Thus, if this system can express β-galactosidase into the egg, then other genes will likewise be expressed. Second, β-galactosidase expression can be easily assayed, which facilitates screening of eggs produced from the transgenic hens of the present invention. It will be appreciated that any transgene(s) or fragment thereof, may be employed.

3' Control. Since the transgenic vector of the present invention is a retrovirus, the genome is RNA and, a transcription termination signal in the orientation of genome synthesis could prematurely stop synthesis and result in low titers of retrovirus. Other investigators have used termination and polyadenylation signals and found relatively little effect. Bradyopadhy, P. K., et al., *Mol. Cell Biol.* 4(4):749–754 (1984). A transcription termination signal should not disrupt genome synthesis if placed in the opposite orientation, however, but may not benefit from the enhancing effect of a more proximal LTR in the retroviral vector. Therefore, both orientations of the expression vector with respect to the retroviral vector were constructed. Standard stop codons and the proven polyadenylation signal from the SV40 small T antigen are included 3' to the structural gene.

Materials and Methods

Figure 3:
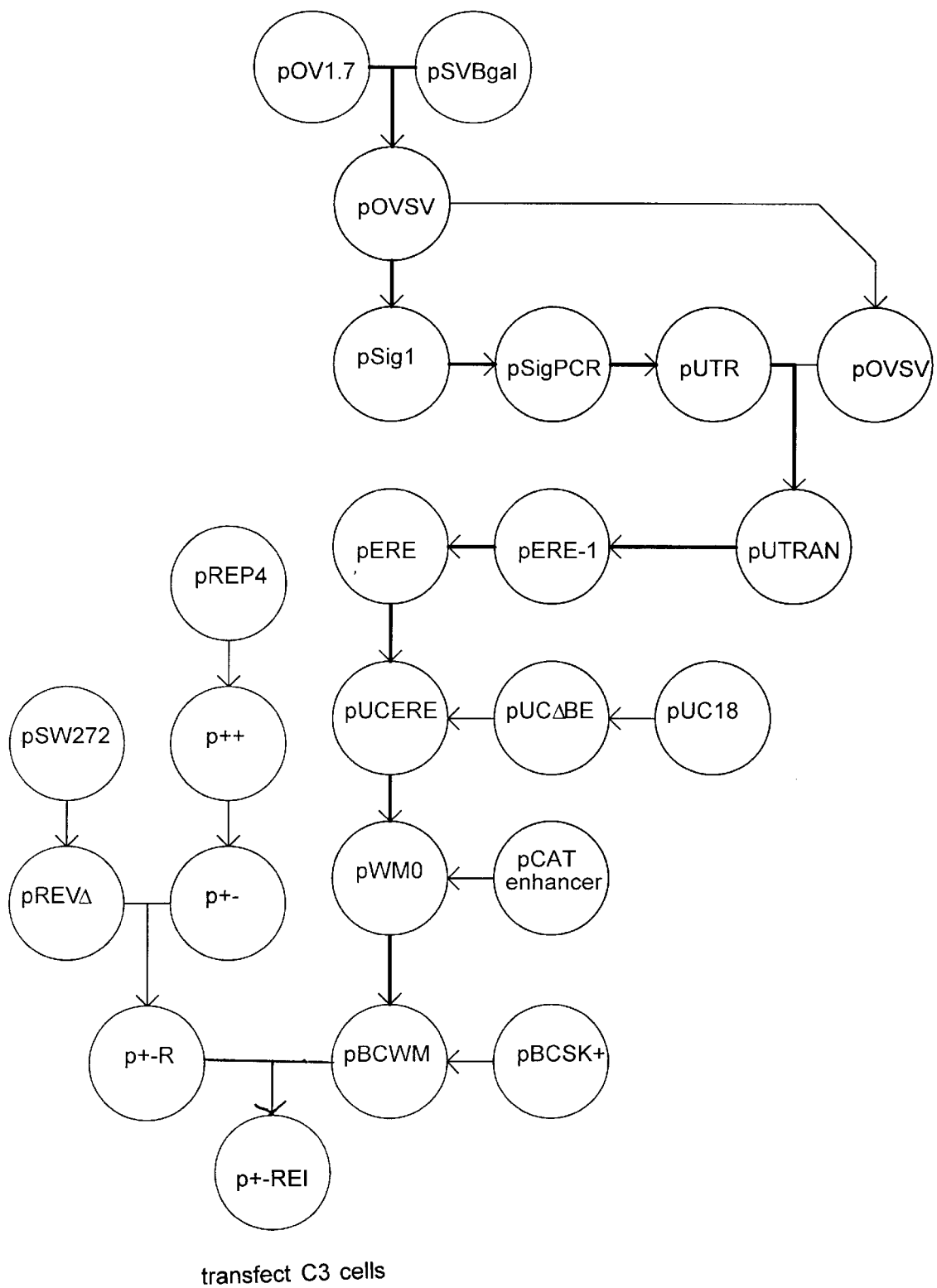
FIG. 3 is a schematic illustrating construction of the retroviral and expression vectors of the present invention.

Introduction. The β-galactosidase gene together with transcription termination signals and the polyadenylation signal from the SV40 small T antigen are contained on a 3.5 kb Cla I-Xba I fragment of the expression vector pSVβ-galactosidase, purchased from Promega Inc. The ovalbumin promoter is contained on a 1.7 kb Pst I Eco RI fragment of the plasmid pOV1.7 (sequence in Helig, R., et al., *J. Mol. Biol.* 156:1–19 (1982), Genback accession # J00895 M24999). The SV40 enhancer is contained on a 247 bp Nco I—Eco RI fragment of the plasmid pCAT-enhancer, purchased from Promega Inc. All other DNAs in the construct were synthesized de novo. FIG. 3 is a schematic illustrating the construction of the retroviral and expression vectors.

Figure 4:
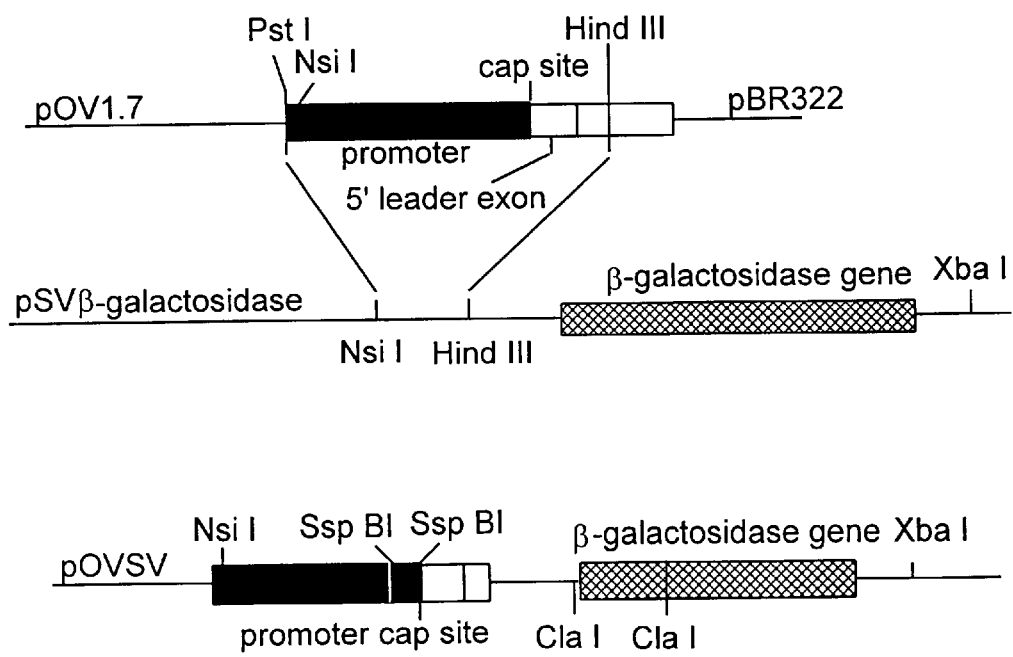
FIG. 4 is a schematic illustrating the construction of intermediate #1, pOVSV.

Construction of intermediate #1; pOVSV. The plasmid pOV1.7 contains a Hind III site in the first intron of the ovalbumin gene, and a Pst I site 1.37 kb 5' to the cap site (see FIG. 4). This 1.6 kb Pst I Hind III fragment of pOV1.7 was joined to the Hind III and Nsi I sites of pSVβ-galactosidase, (Nsi I has compatible ends with Pst I), resulting in a plasmid called pOVSV, shown in FIG. 4. pOVSV is the first of 8 intermediates generated to construct the most complex version of the vector.

Figure 5:
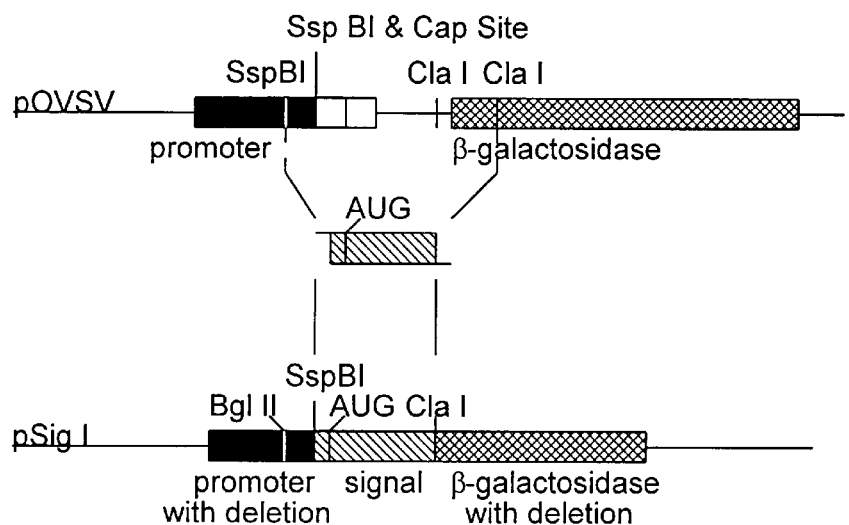
FIG. 5 is a schematic showing the construction of intermediate #2, pSigI (SEQ ID Nos. 2–7)

Construction of intermediate #2; pSigI. A synthetic linker containing the nucleotide sequence encoding the signal peptide from chicken lysozyme was inserted into the Ssp BI and Cla I sites of pOVSV as shown in FIG. 5. The resulting plasmid is called pSigI. The nucleotide sequence is included in FIG. 5, along with the amino acid sequence of the signal peptide and the start codon.

Figure 6:
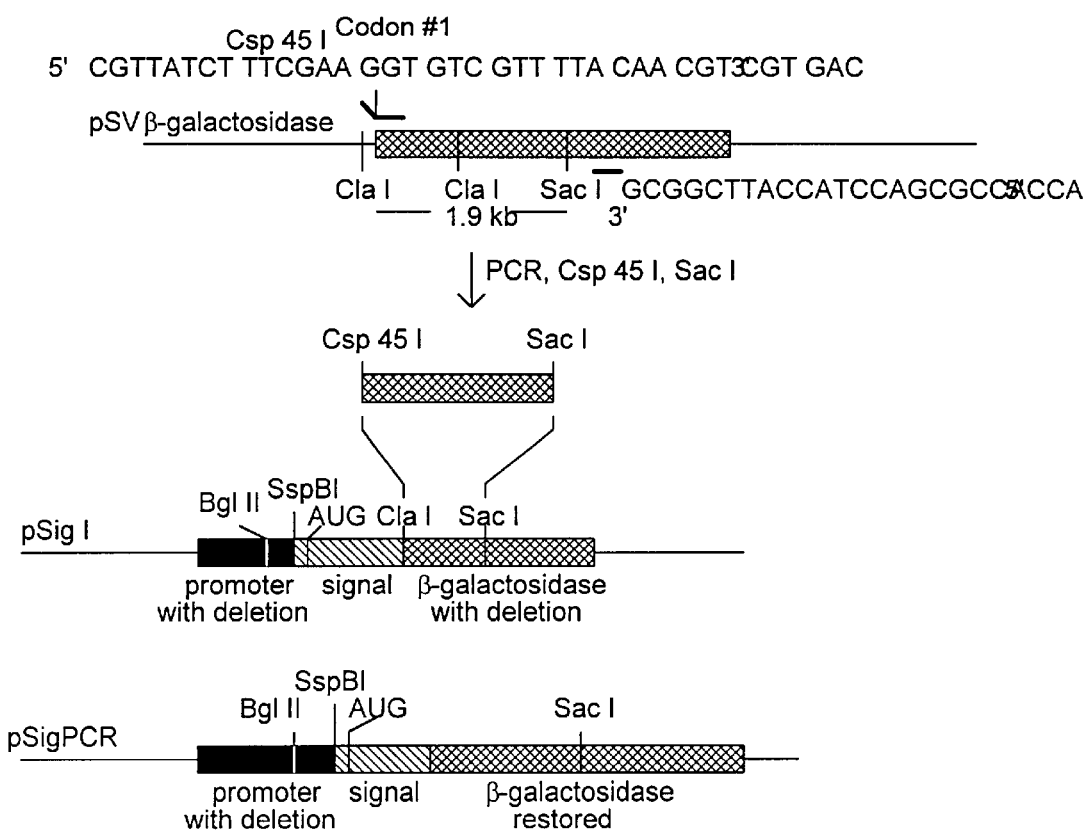
FIG. 6 is a schematic illustrating the construction of intermediate #3, pSigPCR (SEQ ID NOS 8–9)

Construction of intermediate #3; pSigPCR. The plasmid pSig I contains undesirable deletions in the 3' end of the ovalbumin promoter and in the 5' end of the β-galactosidase gene. The β-galactosidase gene was restored using PCR. A 3' primer was used that hybridizes 35 bp 3' to a unique Sac I site within the gene. Its sequence and the design of the PCR are shown in FIG. 6. The 5' primer hybridizes to the 5' end of the β-galactosidase gene and contains a 17 base 5' overhang containing a unique Csp 45 I site and eight 5' nucleotides. Csp 45 I digestion generates end compatible with Cla I digestion. PCR was performed for 30 cycles, and the products were digested with Sac I and Csp 45 and then purified on a low-melt gel. This 1.9 kb fragment was ligated into the unique Cla I and Sac I sites of psig 1, restoring the β-galactosidase gene and putting it directly 3' to and in frame with the signal sequence codons (see FIG. 6). This plasmid is called pSigPCR, and was verified by Pvu I digestion, and subsequent sequence analysis.

Figure 7:
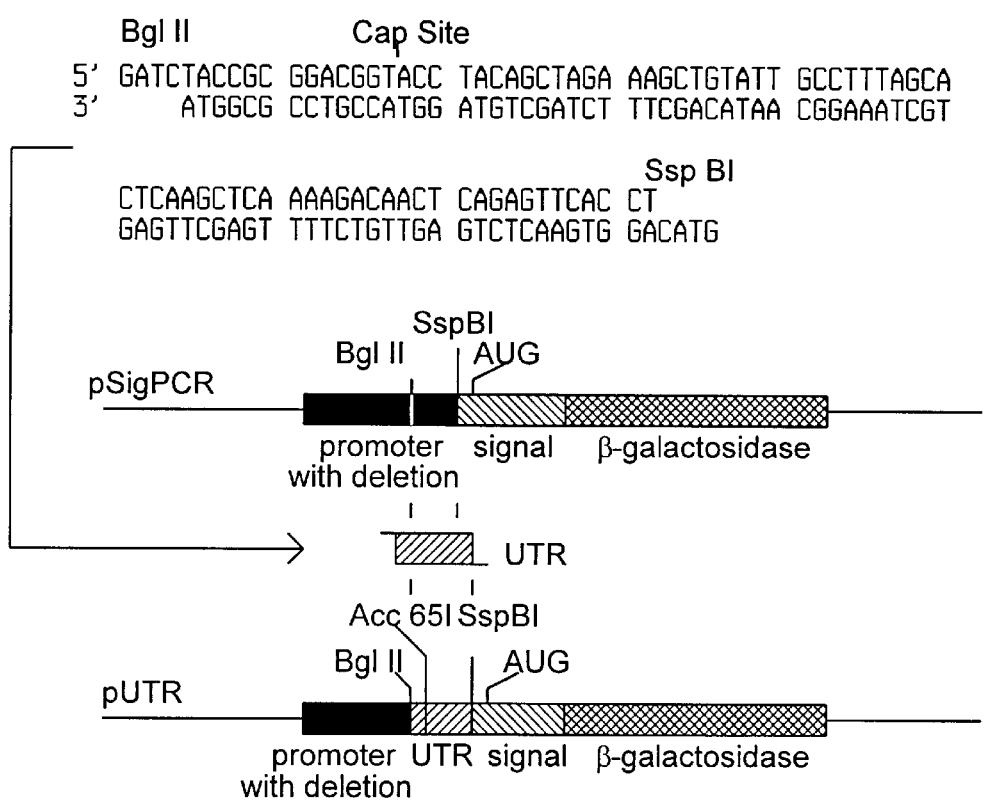
FIG. 7 is a schematic showing the construction of intermediate #4, pUTR (SEQ ID Nos. 10–11)

Construction of intermediate #4; pUTR. A synthetic oligonucleotide encoding the 5' UTR of ovalbumin was ligated into the Bgl II Ssp BI sites of pSigPCR. This oligonucleotide also contains an Acc 65 I site near its 5' end (centered around the cap site) to allow restoration of the promoter in the following steps (see FIG. 7). Proper constructs were verified by Kpn I digestion. This plasmid is called pUTR, and contains all necessary elements 3' to the cap site.

Figure 8:
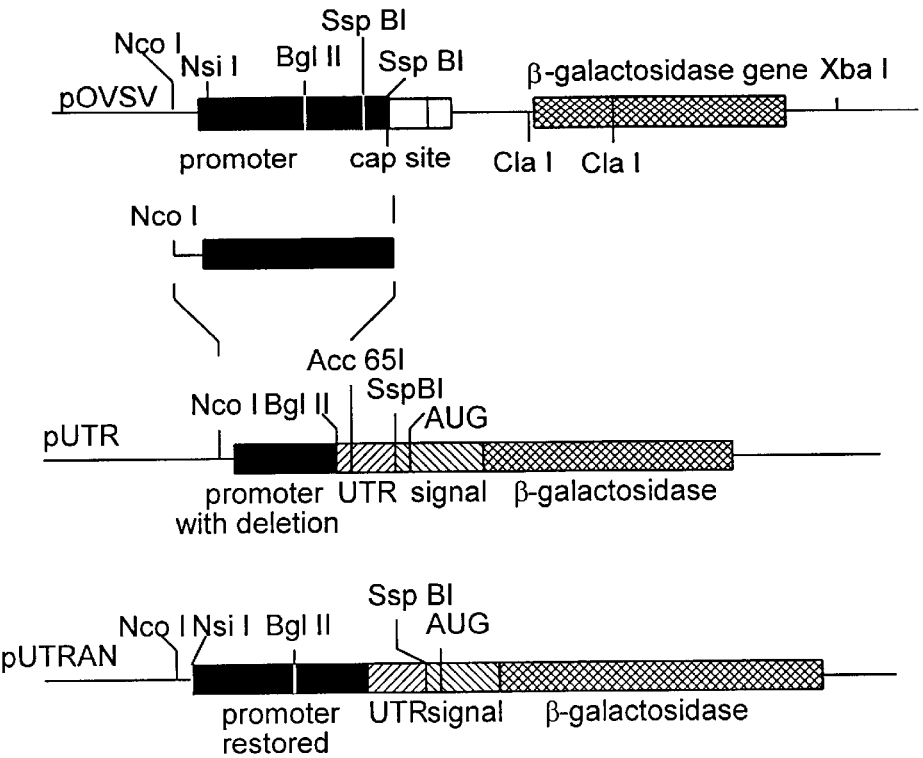
FIG. 8 is a schematic illustrating the construction of intermediate #5, pUTRAN (SEQ ID Nos. 14–15)

Construction of intermediate #5; pUTRAN. The promoter was restored by ligating a 1.4 kb Ssp BI partial—Nco I restriction fragment containing the entire intact promoter from pOVSV into the Nco I and Acc 65 I sites of pUTR, shown in FIG. 8. Proper recombinants were verified by Bgl II Ssp BI double digestion. This plasmid, pUTRAN, has a 1.3 kb ovalbumin promoter driving all necessary downstream elements of the construct.

Figure 9:
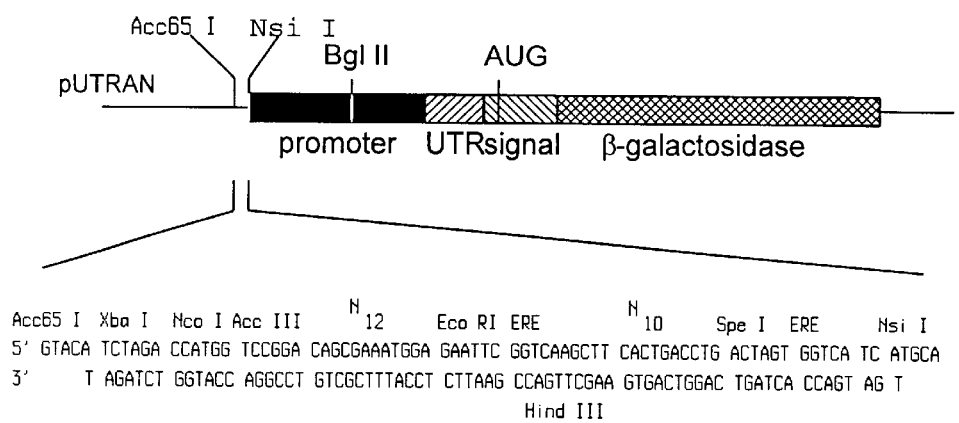
FIG. 9 is a schematic showing the construction of intermediate #6, pERE 1.
Figure 9:
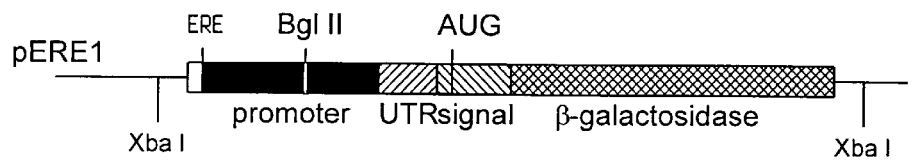
Figure 10:
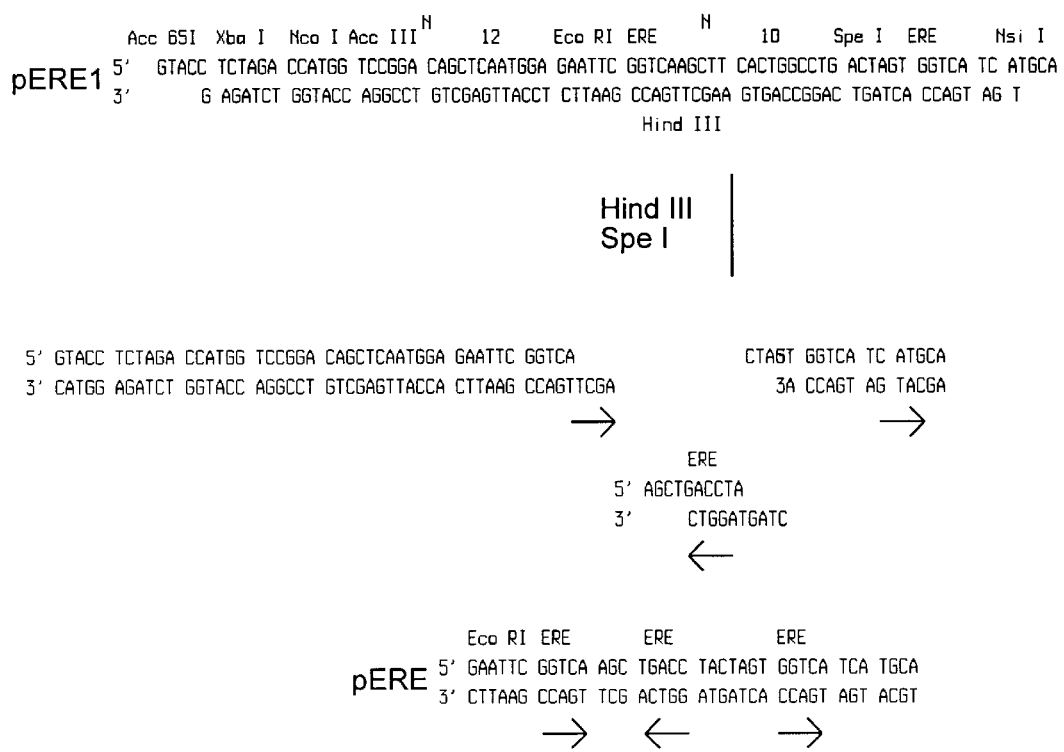
FIG. 10 is a schematic showing the construction of intermediate #7, pERE (note in FIG. 10 that arrows are for orientation of the ERE sequence within the oligonucleotides, not the oligonucleotide itself) (SEQ ID Nos. 16–25)
Figure 11:
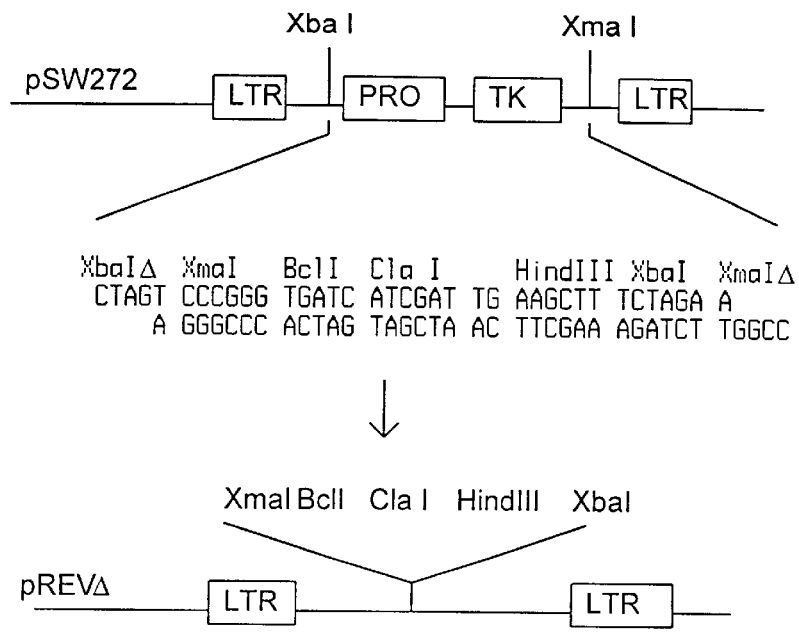
FIG. 11 is a schematic illustrating the modified proviral vector (SEQ ID Nos. 26–27)

Construction of intermediate #6; pERE 1. The tandem estrogen response elements (ERE) are contained on a synthetic oligonucleotide. Because the invested repeats contained within the EREs form stem loop structures which prevent annealing into a double stranded structure, the oligonucleotide was inserted in two steps. The first oligonucleotide contains two EREs in the same orientation, separated by unique Hind III and Spe I sites. This oligonucleotide was ligated into the unique Nsi I and Nco I sites of pUTRAN, forming the plasmid pERE 1. pERE 1 also contains Acc III and Nco I sites useful for insertion of the SV40 enhancer, and a terminal Xba I site to allow insertion of subsequent constructs into the unique Xba I site of the retroviral vector. Proper recombinants were verified by Xba I digestion and sequence analysis Construction of intermediate #7; pERE. A full palindromic ERE was created by ligation of a synthetic oligonucleotide containing the 3' half site into the unique Hind III and Spe I sites of pERE. The resulting plasmid, pERE, contains a full palindromic ERE and a single ERE half site spaced 7 base pairs away (see FIGS. 9 and 10). Proper recombinants were verified by Hind III Bgl II double digestion, since ligation of the second oligonucleotide obliterates the unique Hind III site.

Construction of intermediate #8; pUCERE. The plasmid pERE contains all elements of the expression vector except the SV40 enhancer. The SV40 enhancer is contained on a 247 bp Eco RI Nco I fragment of the plasmid pCAT-enhancer, available from Promega. pERE contains 3 Eco RI sites and 2 Nco I sites, necessitating its subcloning into a vector which lacks these sites.

The plasmid pUC18 contains only one Eco RI sites and lacks an Nco I site altogether. pUC18 was digested with Eco RI and Bam HI (both in the multiple cloning site), blunted with Klenow polymerase, and autoligated. Proper deletions were verified by Eco RI—Sca I double digestion. The modified vector is called pUCΔBE, and contains a unique Xba I site useful in subcloning the construct. Subsequently, the 5 kb Xba I fragment of pERE, containing the construct, was ligated into the modified vector at that site. This plasmid is called pUCERE.

Construction of pWM0. pUCERE contains Nco I and Eco RI sites 5' to the EREs, and 3' to the Xba I site necessary for subcloning into the retroviral vector. It also contains an extra Eco RI site within the β-galactosidase gene, which necessitates a partial digestion strategy. pUCERE was partially digested with Eco RI, and the linear band isolated. This DNA was digested with Nco I, and the 8 kb fragment recovered from a low-melt gel. The 247 bp Eco RI—Nco I fragment of pCAT-enhancer was isolated by standard means, and ligated to the pUCERE preparation. Proper recombinants were verified by Xba I—Bgl II double digestion. This plasmid is called pWV0, and contains all elements of the transgene on a 5 kb Xba I fragment.

Construction of pBCWM. pWM0 and pSW272 both confer ampicillin resistance to their hosts. To reduce the level of background plasmid when subcloning into the ampicillin resistant REV vectors, the 5 kb insert of pWM0 was cloned into the unique Xba I site of pBCSK+, purchased from Stratagene (La Jolla, Calif.), which confers chloramphenicol resistance to its host. pWM0 was digested with Xba I, and the 5 kb fragment isolated from a low melt gel. pBCSK+ was digested with Xba I, dephosphorylated, and purified on agarose. The vector and insert fragments were ligated together, and proper recombinants were verified by Xba I digest on cultures grown from colonies recovered from LB chloramphenicol (34 μg/ml) plates. This plasmid contains the entire expression vector on a background of chloramphenicol resistance, ready for insertion into the replication defective retroviral vector.

SPECIFIC EXAMPLE 2

Retroviral Vector Design and Construction

Retroviral Vector Design

The plasmid pSW272 (Emerman and Temin, Cell 39:459–467 (1984)) contains a deletion mutant of spleen necrosis virus (SNV), now the reticuloendotheliosis virus (REV). The provirus within the plasmid comprises the LTRs, the packaging sequence and the thymidine kinase gene and its promoter as a selectable marker for determination of viral titer. There is a unique Xba I site 5' to the thymidine kinase promoter. In a previous study, the neomycin phosphotransferase gene had been inserted in this vicinity (in a Hind III site) resulting in a second construct pME 111 (Emerman and Temin, Cell 39:459–467 (1984)) which was used successfully to generate a transgenic chicken (Bosselman, et al., Science 243:533–535 (1989)). In the same study, the gene encoding chicken growth hormone was cloned into pSW272, and resulting transgenic chickens had significantly higher levels of circulating growth hormone than nontransgenic controls. pSW272 was modified to better serve as a vehicle for the expression vector.

The goals in modifying the retroviral architecture include: replacement of the thymidine kinase gene with the gene conferring resistance to hygromycin B (this eliminates the need for co-transfection, however, it also requires remodeling the ends of the hygromycin gene); elimination of the 5' promoter driving the hygromycin gene, and its polyadenylation signal (this will provide a more stable architecture); and provide an Xba I site 3' to the hygromycin gene for insertion of the expression vector. pSW272 was reconstructed in three phases. The first phase was the deletion of the herpes virus thymidine kinase promoter and structural gene, and replacement with a synthetic linker. This linker contains sites necessary for subsequent manipulations, including a unique Xba I site at the 3' end which allows insertion of the 5 kb expression construct contained in pBCWM. The second phase was the introduction of linkers at the 5' and 3' ends of the hygromycin resistance gene that allow for more specific construction of control sequences at the ends of the gene. The third phase tested 4 different arrangements of control sequences for their ability to stably transfect the C3 cell line. The arrangement with the fewest control sequences that can stably transfect the C3 cells was chosen as a preferred proviral vector.

The retroviral vector pSW272 contains the reticuloendotheliosis virus (REV) long terminal repeats (LTR)s, and also the selectable marker thymidine kinase (TK) driven by its own promoter. The LTRs lie at the ends of the provirus, and can function as promoters.

By itself, pSW272 is a stable architecture, stable in this case referring to the ability to generate full length retrovirus with no internal deletions from its genome. The selectable marker is useful for titering retrovirus on TK⁻ cells, but not helpful for transfecting the helper cells necessary to generate the retrovirus.

Additionally, problems may arise when the expression vector is inserted into pSW272, and the entire construct is then transfected into the C3 cell line. The structure of the construct then includes two internal promoters. The 5' or left promoter (in this case the ovalbumin promoter) may be unstable in this environment, meaning retrovirus produced from cells transfected with such a construct experience frequent deletions in this region (Emerman and Temin, J. Virology 50(1):42–49 (1984)).

The same study provided evidence that a structural gene alone in that location is stable and can be expressed by the LTR, eliminating the need for a promoter. Since that gene can be virtually any structural gene, it can be the selectable marker. The C3 packaging cell line contains endogenous Tk activity and consequently it must be co-transfected with a plasmid conferring hygromycin B resistance. The gene encoding hygromycin B phosphotransferase was cloned into the retroviral vector to generate an improved architecture.

The expression vector was then inserted at the unique Xba I site, resulting in a stable architecture, elimination of the need for co-transfection and still enabling the titration of virus on CEF cells.

Retroviral Vector Construction

Construction of pREVΔ. A schematic illustrating the construction of the retroviral vector is set forth in FIG. 3. The promoter and structural gene of thymidine kinase are carried on a 2 kb Xba I—Xma I fragment, both of which are unique in pSW272. pSW272 was digested with Xba I and Xma I, and the larger fragment (approximately 7 kb) recovered from a low melt gel. This fragment was ligated to a synthetic oligonucleotide containing 5 restriction sites. The resulting construction, pREVΔ, was confirmed by Cla I digestion, as Cla I recognizes a site in the synthetic linker, and a second site outside of the proviral DNA.

Modification Of Hygromycin B Phosphotransferase Gene

Modification to pREP4. The hygromycin B phosphotransferase gene is contained on the plasmid pREP-4, purchased from Invitrogen. However, there are problems with the hygromycin B phosphotransferase gene at both the 5' and 3' ends. At the 5' end, there is an unfavorable sequence surrounding the start codon, specifically a second out-of-frame start codon 4 bp upstream. The 3' end contains both a polyadenylation signal, which may interfere with retroviral titer, and the LTR from Raus Sarcoma Virus (RSV), which must be removed. The 3' end also lacks convenient restriction sites necessary to generate the desired constructs, and with the remodeling, these sites are included.

The plasmids are named after the nature of their control signals. For example, the construct containing both a promoter and a polyadenylation signal is designated p++. Similarly, the plasmid containing a promoter, but no polyadenylation signal is called p+−.

Figure 12:
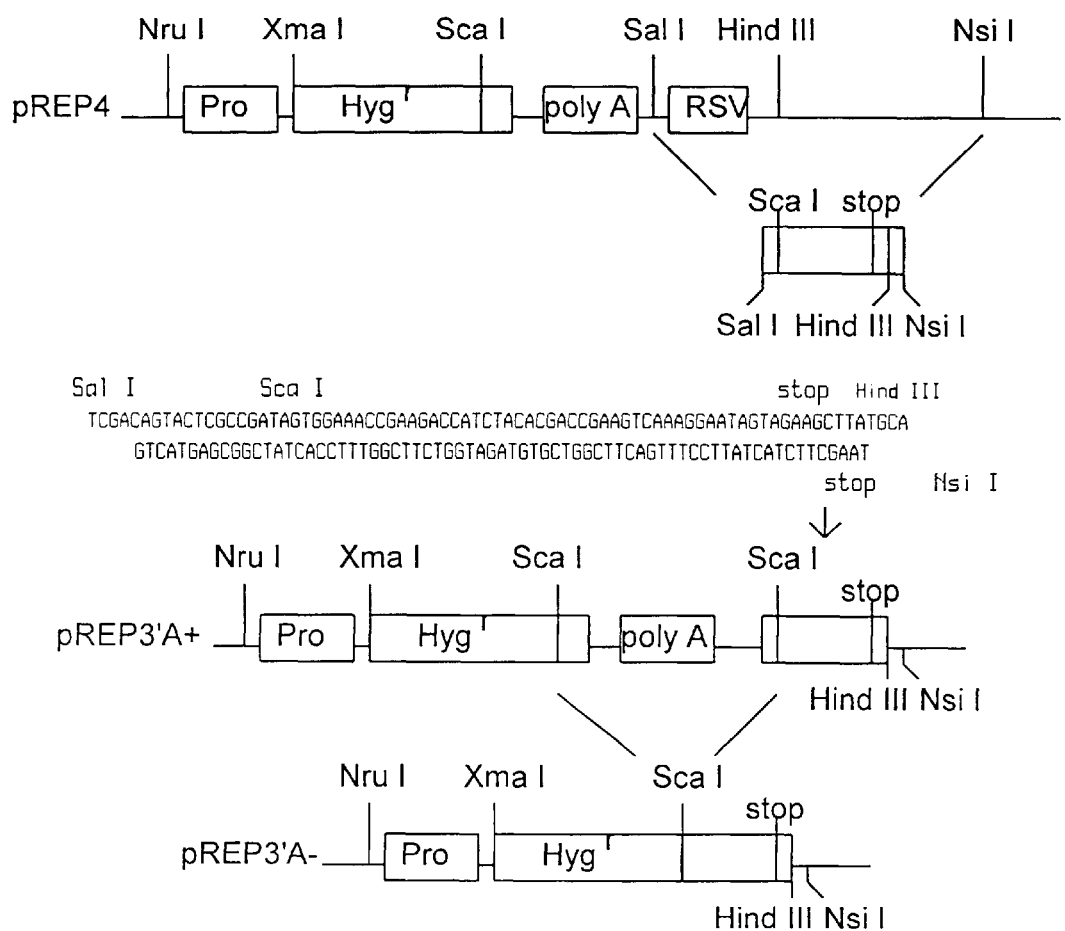
FIG. 12 is a schematic illustrating the modification of the 3' end of the hygromycin B phosphotransferase gene; (SEQ ID Nos. 12–13)

Construction of p++. The 3' end of the hygromycin B phosphotransferase gene was modified using synthetic double stranded oligos. FIG. 12 shows the modification of the 3' end of the Hyg gene. A unique Sca I site located 60 bp from the stop codon, within the gene (see FIG. 12). A synthetic oligonucleotide containing a Sca I site, the C-terminal codons and stop codon of the hygromycin marker gene, a Hind III site and flanking Nsi I and Sal I ends was cloned into the Nsi I and Sal I sites on pREP4. Proper recombinants were verified by HindIII—Nru I double digestion, and are called p++.

Construction of p+−. p++ was partially digested with Sca I and the 6.3 kb fragment recovered from a low melt gel and autoligated, resulting in a hygromycin gene construct lacking 3' control elements except the stop codons (see FIG. 12). Proper recombinants were verified by Sca I—Cla I double digestion, and called p+−.

Figure 13:
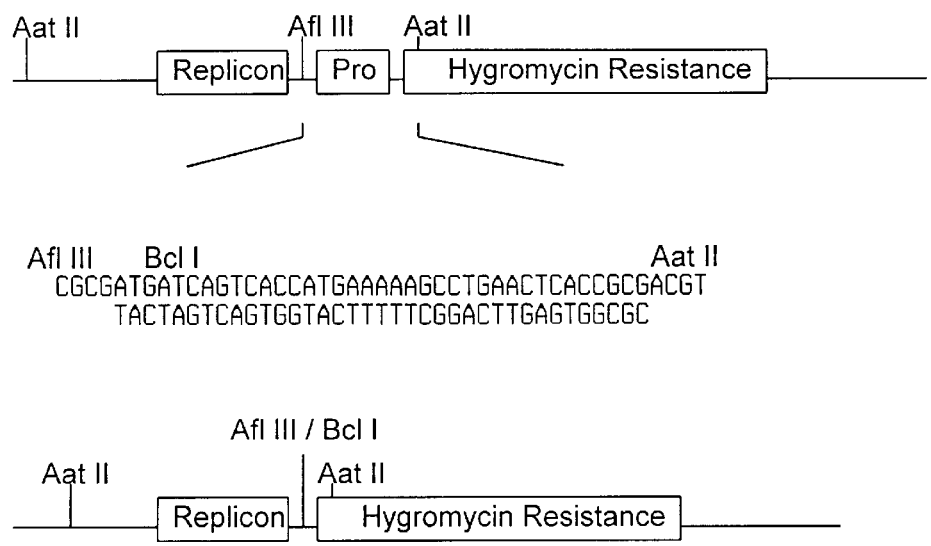
FIG. 13 is a schematic showing the modification of the N-terminus of hygromycin B phosphotransferase gene (SEQ ID Nos. 28–29).

Construction of p−+ and p−−. The N-terminal codons were modified in a similar manner. Afl III is unique in p++, and lies just 5' to the start codon of the hygromycin B phosphotransferase gene. An Aat II site lies 25 bases into the hygromycin gene, making an Afl III—Aat II double digestion convenient for removal of the promoter. Aat II is not unique to p++, and thus a two enzyme strategy was used. p++ was digested with Cla I and Aat II and in a separate reaction Cla I and Afl III. The digestion products were run on a low melt gel, and the 5.5 kb Cla I Aat II product recovered, and the 2.4 kb Cla I Afl III product recovered. These two DNAs were ligated with a synthetic oligonucleotide (see FIG. 13) resulting in p−+. Proper recombinants were verified by Bcl I Alw NI double digestion and sequence analysis. The plasmid p+− was treated the same way, resulting in the plasmid p−−.

The manipulation to the N-terminal portion of the gene was done independently for p++, and p+−. The resulting four constructs contain all the permutations for the control signals as: 1) with promoter, with poly A signal—contained on an Nru I—Hind III fragment of p++; 2) with promoter, without poly signal—contained on an Nru I—Hind III fragment of p+−; 3) without promoter, with poly A signal—contained on a Bcl I—Hind III fragment of p−+; and 4) without promoter, without poly A signal—contained on an Bcl I—Hind III fragment of p−−.

The fragments with promoters (1 and 2 above) were cloned into pREVΔ at the Sma I (Xma I) and Hind III sites in the multiple cloning site. Since recircularization secondary to incomplete digestion is always a concern, the plasmid pREVΔ was digested at three sites: Sma I, Hind III, and Acc III. Recovery of the 2 fragments of the appropriate size from low melt gels ensured digestion at both sites within the MCS, and when ligated to the Nru I—Hind III fragments in a 3-molecule ligation, resulted in desired plasmid readily. These plasmids are called p++R and p+−R.

A similar procedure was used to clone the hygromycin B phosphotransferase gene without a promoter into REV. The hygromycin constructs (p−+ and p−−) were digested with Bcl I and Hind III, and cloned in a 3 molecule ligation to gel purified Bcl I, Hind III, and Acc III fragments of pREVΔ, and called p−+R and p−−R.

The insertion of the expression vector into these retroviral vectors is as follows. Each retroviral vector contains a unique Xba I site. The appropriate plasmid was opened with Xba I, dephosphorylated, and gel purified. pBCWM contains the expression vector on a chloramphicicol resistant plasmid as a 5 kb Xba I fragment. pBCWM was digested with Xba I and the 5 kb fragment recovered from a low melt gel and ligated to the appropriate retroviral vector. Proper recombinants were verified by Xba I digestion, and orientation was checked by Eco RI digestion. These plasmids were named as for their retroviral vectors, with the addition of E and the clone number. For instance: p++RE1, with promoter, with poly adenylation, in REV and with expression vector in orientation 1.

SPECIFIC EXAMPLE 3

Transgenesis

Method 1

Each of the two orientation constructs for a given retroviral vector, was transfected into the C3 cell line, and stable clones selected. DNA is isolated from the clones and analyzed for integrated intact proviral DNA by Southern blot. Appropriate clones are propagated and assayed for retrovirus on CEF cells selected for hygromycin resistance. Clones producing high titers are used to generate retrovirus, which is further concentrated by filtration and/or centrifugation.

When a clone is found producing high titers of intact viral DNA, eggs are injected as described in U.S. Pat. No. 5,162,215 and Bosselman, R. A. et al., Science 243:533–535 (1989), herein incorporated by reference. Newly laid line 0 SPF eggs are obtained from SPAFAS (Preston, Conn.), and maintained at 20° C. on one side for at least 5 hours. The top of the egg is prepped with 70% ethanol, and air dried. The shell is then opened with a dremmel mototool fitted with a steel burr. 15–25 microliters of a solution containing retrovirus is microinjected beneath the blastoderm. The eggs are sealed and incubated in a Humidaire incubator until hatching.

Ten days after hatching, blood is collected from the chicks, and assayed for the presence of viral DNA in their genomes by Southern blot and PCR. All chickens are grown to maturity, at which time, the eggs of these chimeric chickens are tested for the presence of β-galactosidase, and the rooster semen is tested for viral DNA by Southern blot. Semen positive roosters are used to sire G2 chickens which are true heterozygous transgenic chickens.

Method 2

The 5 kb insert (the expression vector) of pBCWM was ligated to pREVΔ or p+−, cut with Xba I, dephosphorylated and purified on a low melt gel. Clones were screened for the insert by Xba I digestion, and orientation was checked by digestion with Eco RI.

C3 cells were seeded at 2–3×10$^5$ cells per well in a 6 well plate (35 mm well diameter) and grown overnight in DMEM with high glucose supplemented with L-glutamine, 10 mM HEPES, 7% calf serum, 400 μg/ml G-418, 100 μg/ml gentamicin, 5 μg/ml fungizone (amphotericin B), 100 units/ml penicillin G, 100 μg/ml streptomycin sulfate, at 37° C. in 10% CO$_2$. The cells were transfected using lipofectamine (Gibco Life Technologies) at a ratio of 1.5 μg DNA to 8 ul lipofectamine, according to the manufacturer's specifications. After 5 hours the transfection medium was aspirated and replaced with 0.5 ml of DMEM with 7% calf serum, and HEPES. The medium was removed after 48 hours of incubation and used for microinjection or concentrated by ultrafiltration 20-fold with a filter with a 50 kd cut-off and used for microinjection.

Newly laid fertilized SPF white leghorn eggs were obtained from SPAFAS and maintained on their side for at least 5 hours. A pentagonal shaped piece of shell approximately 0.5 cm$^2$ was removed intact from the top-most portion of the egg using a Dremmel mototool fitted with a steel cutter (part 113). The shell membrane was removed with an 18 gauge needle. Micropipettes were pulled on a Sutter puller, trimmed with a razor blade, and checked for diameter and tip angle under a microscope. 15 to 20 μl of medium was injected into the subgerminal space using a Narishige micromanipulator (model MN-151) and microinjector (model IM-6). The hole was patched using donor membranes harvested from eggs in the same lot held briefly in PBS with penicillin G and streptomycin sulfate used at the concentrations stated above. The shell fragment was replaced on top of the donor membrane, and air dried for 10 minutes. Duco cement was used to seal the edges, and air dried for at least 30 minutes. The eggs were then set in a Humidaire incubator (model 21) and hatched according to manufacturers specifications.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

All patents and other publications cited herein are expressly incorporated by reference.

We claim:

1. A chimeric chicken comprising a transgene and control elements operatively-linked to the transgene, wherein the control elements comprise a portion of an ovalbumin promoter as defined by positions 284–1619 of SEQ ID NO: 1, an SV40 enhancer, three estrogen response elements, an ovalbumin gene 5' untranslated region, and an egg white lysozyme signal sequence, wherein said chimeric chicken expresses the transgene such that a protein encoded by the transgene is produced in the egg white of an egg made by the chimeric chicken.

2. A method for producing a chicken chimeric for a transgene comprising the steps of:
   a) making an opening in an unincubated chicken egg which contains an embryo, so as to expose a blastoderm;
   b) microinjecting through the opening into an area in close proximity to the blastoderm, a solution containing a replication-defective recombinant retrovirus comprising the transgene and control elements operatively-linked thereto, wherein the control elements comprise a portion of an ovalbumin promoter as defined by positions 284–1619 of SEQ ID NO: 1, an SV40 enhancer, three estrogen response elements, an ovalbumin gene 5' untranslated region, and an egg white lysozyme signal sequence;
   c) sealing the opening after microinjection; and
   d) incubating the egg until the chimeric chicken is hatched from the egg, wherein said chimeric chicken expresses the trans gene such that a protein encoded by the transgene is produced in the egg white of an egg made by the chimeric chicken.

3. The method of claim 2, wherein the replication-defective recombinant retrovirus is generated with a retroviral vector derived from REV-A.

4. A chimeric chicken produced by the method of claim 2.

5. A chimeric embryonic chicken cell produced by introducing a replication-defective recombinant retrovirus into the cell, wherein the recombinant retrovirus comprises the transgene and control elements operatively-linked thereto, wherein the control elements comprise a portion of an ovalbumin promoter as defined by positions 284–1619 of SEQ ID NO: 1, an SV40 enhancer, three estrogen response elements, an ovalbumin gene 5' untranslated region, and an egg white lysozyme signal sequence, wherein a chimeric chicken produced from the embryonic chicken cell expresses the transgene such that a protein encoded by the transgene is produced in the egg white of an egg made by the chimeric chicken.

6. A method for transferring a transgene to an embryonic chicken cell, comprising the step of introducing a replication-defective recombinant retrovirus into the cell, wherein the recombinant retrovirus comprises the transgene and control elements operatively-linked thereto, wherein the control elements comprise a portion of an ovalbumin promoter as defined by positions 284–1619 of SEQ ID NO: 1, an SV40 enhancer, three estrogen response elements, an ovalbumin gene 5' untranslated region, and an egg white lysozyme signal sequence, wherein a chimeric chicken produced from the embryonic chicken cell expresses the transgene such that a protein encoded by the transgene is produced in the egg white of an egg made by the chimeric chicken.

7. The method of claim 6, wherein the replication-defective recombinant retrovirus is generated with a retroviral vector derived from REV-A.

* * * * *

SEQUENCE LISTING (1) GENERAL INFORMATION:

(iii) NUMBER OF SEQUENCES: 29

(2) INFORMATION FOR SEQ ID NO: 1:

(i) SEQUENCE CHARACTERISTICS:
      (A) LENGTH: 1753 base pairs
      (B) TYPE: nucleic acid
      (C) STRANDEDNESS: single
      (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 1:

```
TCTAGACCAT GGAGCGGAGA ATGGGCGGAA CTGGGCGGAG TTAGGGGCGG GATGGGCGGA      60

GTTAGGGGCG GGACTATGGT TGCTGACTAA TTGAGATGCA TGCTTTGCAT ACTTCTGCC      120

GCTGGGGAGC CTGGGGACTT TCCACACCTG GTTGCTGACT AATTGAGATG CATGCTTTG     180

ATACTTCTGC CTGCTGGGGA GCCTGGGGAC TTTCCACACC CTAACTGACA CACATTCCA     240

AGCAGATCCC CCGGAATTCG GTCAAGCTGA CCTACTAGTG GTCATCATGC ATTTCATAG     300

TAGAGATAAC ATTTACTGGG AAGCACATCT ATCATCACAA AAAGCAGGCA AGATTTTCA     360

ACTTTCTTAG TGGCTGAAAT AGAAGCAAAA GACGTGATTA AAAACAAAAT GAAACAAAA     420
```

```
AAATCAGTTG ATACCTGTGG TGTAGACATC CAGCAAAAAA ATATTATTTG CACTACCAT       480

TTGTCTTAAG TCCTCAGACT TGGCAAGGAG AATGTAGATT TCCACAGTAT ATATGTTTT       540

ACAAAAGGAA GGAGAGAAAC AAAAGAAAAT GGCACTGACT AAACTTCAGC TAGTGGTAT       600

GGAAAGTAAT TCTGCTTAAC AGAGATTGCA GTGATCTCTA TGTATGTCCT GAAGAATTA       660

GTTGTACTTT TTTCCCCCAT TTTTAAATCA AACAGTGCTT TACAGAGGTC AGAATGGTT       720

CTTTACTGTT TGTCAATTCT ATTATTTCAA TACAGAACAA TAGCTTCTAT AACTGAAAT       780

TATTTGCTAT TGTATATTAT GATTGTCCCT CGAACCATGA ACACTCCTCC AGCTGAATT       840

CACAATTCCT CTGTCATCTG CCAGGCCATT AAGTTATTCA TGGAAGATCT TGAGGAAC        900

CTGCAAGTTC ATATCATAAA CACATTTGAA ATTGAGTATT GTTTTGCATT GTATGGAGC       960

ATGTTTTGCT GTATCCTCAG AAAAAAAGTT TGTTATAAAG CATTCACACC CATAAAAA1      020

TAGATTTAAA TATTCCAACT ATAGGAAAGA AAGTGTGTCT GCTCTTCACT CTAGTCTC1      080

TTGGCTCCTT CACATGCACG CTTCTTTATT TCTCCTATTT TGTCAAGAAA ATAATAGG1      140

AAGTCTTGTT CTCATTTATG TCCTGTCTAG CGTGGCTCAG ATGCACATTG TACATACA1      200

AAGGATCAAA TGAAACAGAC TTCTGGTCTG TTACTACAAC CATAGTAATA AGCACACT1      260

CTAATAATTG CTAATTATGT TTTCCATCTC CAAGGTTCCC ACATTTTTCT GTTTTCTT1      320

AGATCCCATT ATCTGGTTGT AACTGAAGCT CAATGGAACA TGAGCAATAT TTCCCAGT1      380

TCTCTCCCAT CCAACAGTCC TGATGGATTA GCAGAACAGG CAGAAAACAC ATTGTTAC1      440

AGAATTAAAA ACTAATATTT GCTCTCCATT CAATCCAAAA TGGACCTATT GAAACTAA1      500

TCTAACCCAA TCCCATTAAA TGATTTCTAT GGTGTCAAAG GTCAAACTTC TGAAGGGA1      560

CTGTGGGTGG GTCACAATTC AGACTATATA TTCCCCAGGG CTCAGCCAGT GTCTGTAC1      620

ACAGCTAGAA AGCTGTATTG CCTTTAGCAC TCAAGCTCAA AAGACAACTC AGAGTTCA1      680

TGTTACATAC AGCTATGAGG TCTTTGCTAA TCTTGGTGCT TGCTTCCTG CCCCTGGC1       740

CTCTGGGGAA TAT                                                       1753

(2) INFORMATION FOR SEQ ID NO: 2:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO: 2:

Met Arg Ser Leu Leu Ile Leu Val Leu Cys Phe Leu Pro Leu
 1               5                  10

(2) INFORMATION FOR SEQ ID NO: 3:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 3:
```

```
GTACATACAG CTATGAGGTC TTTGCTAATC TTGGTGCTTT GCTTCCTGCC CCTG      54

(2) INFORMATION FOR SEQ ID NO: 4:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 4:

CAGGGGCAGG AAGCAAAGCA CCAAGATTAG CAAAGACCTC ATAGCTGTAT           50

(2) INFORMATION FOR SEQ ID NO: 5:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 5:

Ala Ala Leu Gly Asn Ile
 1               5

(2) INFORMATION FOR SEQ ID NO: 6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 6:

GCTGCTCTGG GGAATAT                                               17

(2) INFORMATION FOR SEQ ID NO: 7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 7:

CGATATTCCC CAGAGCAGC                                             19

(2) INFORMATION FOR SEQ ID NO: 8:

(i) SEQUENCE CHARACTERISTICS:
        (A) LENGTH: 38 base pairs
```

```
            (B) TYPE: nucleic acid
            (C) STRANDEDNESS: single
            (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 8:

CGTTATCTTT CGAAGGTGTC GTTTTACAAC GTCGTGAC                                    38

(2) INFORMATION FOR SEQ ID NO: 9:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 9:

ACCACCGCGA CCTACCATTC GGCG                                                  24

(2) INFORMATION FOR SEQ ID NO: 10:

(i) SEQUENCE CHARACTERISTICS:
            (A) LENGTH: 82 base pairs
            (B) TYPE: nucleic acid
            (C) STRANDEDNESS: single
            (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 10:

GATCTACCGC GGACGGTACC TACAGCTAGA AAGCTGTATT GCCTTTAGCA CTCAAGCTCA           60

AAAGACAACT CAGAGTTCAC CT                                                    82

(2) INFORMATION FOR SEQ ID NO: 11:

(i) SEQUENCE CHARACTERISTICS:
            (A) LENGTH: 82 base pairs
            (B) TYPE: nucleic acid
            (C) STRANDEDNESS: single
            (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 11:

GTACAGGTGA ACTCTGAGTT GTCTTTTGAG CTTGAGTGCT AAAGGCAATA CAGCTTTCTA           60

GCTGTAGGTA CCGTCCGCGG TA                                                    82

(2) INFORMATION FOR SEQ ID NO: 12:

(i) SEQUENCE CHARACTERISTICS:
```

(A) LENGTH: 77 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 12:

TCGACAGTAC TCGCCGATAG TGGAAACCGA AGACCATCTA CACGACCGAA GTCAAAGGAA      60

TAGTAGAAGC TTATGCA      77

(2) INFORMATION FOR SEQ ID NO: 13:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 13:

TAAGCTTCTA CTATTCCTTT GACTTCGGTC GTGTAGATGG TCTTCGGTTT CCACTATCGG      60

CGAGTACTG      69

(2) INFORMATION FOR SEQ ID NO: 14:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 14:

GTACATCTAG ACCATGGTCC GGACAGCGAA ATGGAGAATT CGGTCAAGCT TCACTGACCT      60

GACTAGTGGT CATCATGCA      79

(2) INFORMATION FOR SEQ ID NO: 15:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 15:

TGATGACCAC TAGTCAGGTC AGTGAAGCTT GACCGAATTC TCCATTTCGC TGTCCGGACC      60

ATGGTCTAGA T      71

(2) INFORMATION FOR SEQ ID NO: 16:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 16:

```
GTACCTCTAG ACCATGGTCC GGACAGCTCA ATGGAGAATT CGGTCAAGCT TCACTGGCCT      60

GACTAGTGGT CATCATGCA                                                  79
```

(2) INFORMATION FOR SEQ ID NO: 17:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 17:

```
TGATGACCAC TAGTCAGGCC AGTGAAGCTT GACCGAATTC TCCATTGAGC TGTCCGGACC      60

ATGGTCTAGA G                                                          71
```

(2) INFORMATION FOR SEQ ID NO: 18:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 18:

```
GTACCTCTAG ACCATGGTCC GGACAGCTCA ATGGAGAATT CGGTCA                    46
```

(2) INFORMATION FOR SEQ ID NO: 19:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 19:

AGCTTGACCG AATTCACCAT TGAGCTGTCC GGACCATGGT CTAGAGGTAC        50

(2) INFORMATION FOR SEQ ID NO: 20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 20:

CTAGTGGTCA TCATGCA        17

(2) INFORMATION FOR SEQ ID NO: 21:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 21:

AGCATGATGA CCA        13

(2) INFORMATION FOR SEQ ID NO: 22:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 22:

AGCTGACCTA        10

(2) INFORMATION FOR SEQ ID NO: 23:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 23:

CTAGTAGGTC        10

(2) INFORMATION FOR SEQ ID NO: 24:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 24:

GAATTCGGTC AAGCTGACCT ACTAGTGGTC ATCATGCA        38

(2) INFORMATION FOR SEQ ID NO: 25:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 25:

TGCATGATGA CCACTAGTAG GTCAGCTTGA CCGAATTC        38

(2) INFORMATION FOR SEQ ID NO: 26:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 26:

CTAGTCCCGG GTGATCATCG ATTGAAGCTT TCTAGAA        37

(2) INFORMATION FOR SEQ ID NO: 27:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 27:

CCGGTTCTAG AAAGCTTCAA TCGATGATCA CCCGGGA        37

(2) INFORMATION FOR SEQ ID NO: 28:

(i) SEQUENCE CHARACTERISTICS:

```
            (A) LENGTH: 45 base pairs
            (B) TYPE: nucleic acid
            (C) STRANDEDNESS: single
            (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 28:

CGCGATGATC AGTCACCATG AAAAAGCCTG AACTCACCGC GACGT                    45

(2) INFORMATION FOR SEQ ID NO: 29:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA genomic (iii) HYPOTHETICAL: NO (iv) ANTI-SENSE: NO (xi) SEQUENCE DESCRIPTION: SEQ ID NO: 29:

CGCGGTGAGT TCAGGCTTTT TCATGGTGAC TGATCAT                             37
```